United States Patent [19]

Shigezawa et al.

[11] Patent Number: 5,357,954
[45] Date of Patent: Oct. 25, 1994

[54] OPTICAL BLOOD OXYGEN SATURATION PROBE FOR INSERTION INTO THE ESOPHAGUS

[75] Inventors: Gordon Shigezawa, Irvine; Anthony V. Beran, Santa Ana, both of Calif.

[73] Assignee: Respiratory Support Products, Inc., Irvine, Calif.

[21] Appl. No.: 91

[22] Filed: Jan. 4, 1993

[51] Int. Cl.$^5$ .............................................. A61B 5/00
[52] U.S. Cl. ................... 128/634; 128/736; 128/715
[58] Field of Search ............... 128/670–671, 128/633–634, 664–667, 736, 715; 356/39–41

[56] References Cited

U.S. PATENT DOCUMENTS

| | | |
|---|---|---|
| 4,383,534 | 5/1983 | Peters .................................. 128/671 |
| 4,619,268 | 10/1986 | Uphold et al. ........................ 128/671 |
| 4,803,992 | 2/1989 | Lemelson ......................... 128/666 X |
| 4,805,623 | 2/1989 | Jobsis . | 
| 4,830,014 | 5/1989 | Goodman et al. ................... 128/665 |
| 5,005,573 | 4/1991 | Buchanan ....................... 128/634 X |
| 5,061,632 | 10/1991 | Shepherd et al. . | 
| 5,263,485 | 11/1993 | Hickey ................................ 128/673 |

Primary Examiner—angela D. Sykes
Attorney, Agent, or Firm—Price, Gess & Ubell

[57] ABSTRACT

A blood oxygen saturation sensor or oximeter is mounted to a probe for insertion into the esophagus of a patient. The sensor includes a set of optical transmission elements and an optical detector for optically detecting the blood oxygen saturation of tissues of the esophagus. By mounting the blood oxygen saturation sensor to a probe for insertion into the esophagus, blood oxygen saturation measurements are obtainable at a physiologically stable site which is fully isolated from ambient light external to the patient. The probe for insertion into the esophagus may additionally be provided with a heart and respiration sound sensor and a temperature sensor. With such a combination, a single probe provides the detection of several useful physiological parameters, including temperature, heart, and respiration sounds and blood oxygen saturation levels. The esophageal probe is reliably and inexpensively constructed of few components and is ideally suited for one-time use.

6 Claims, 2 Drawing Sheets

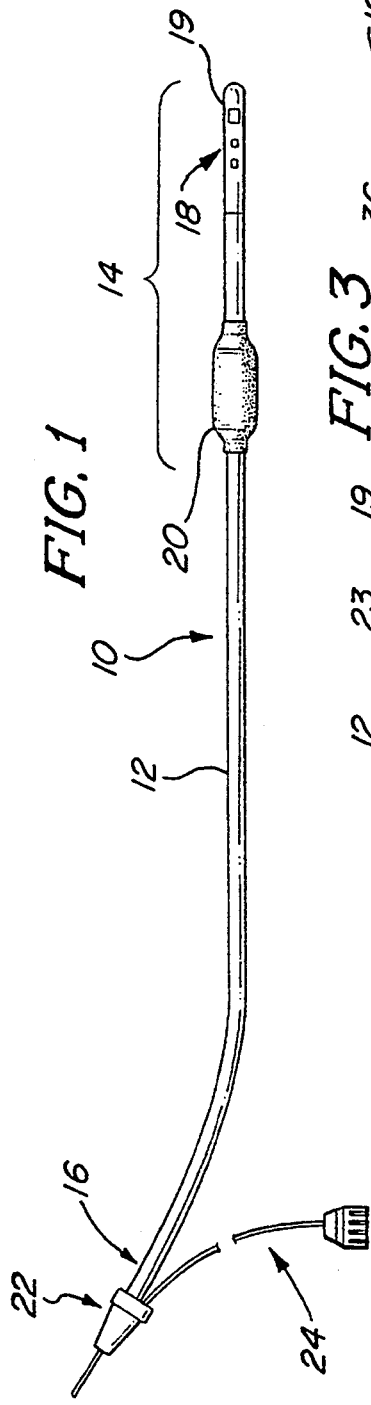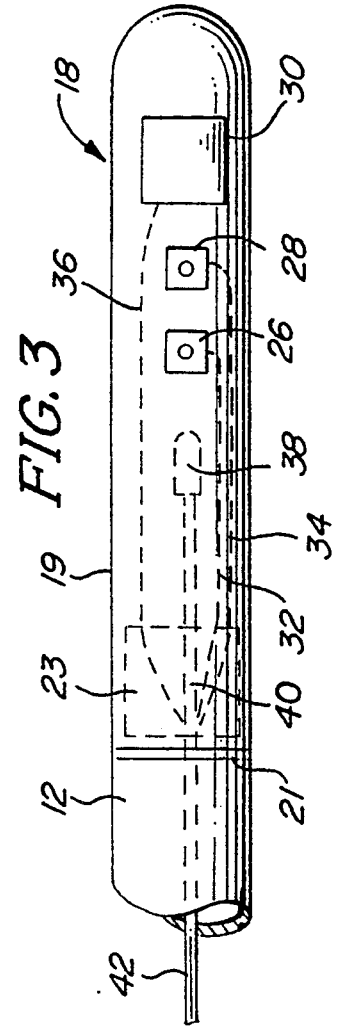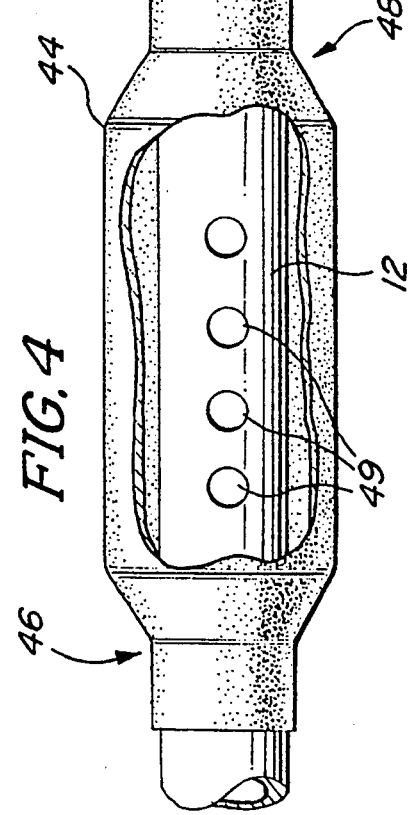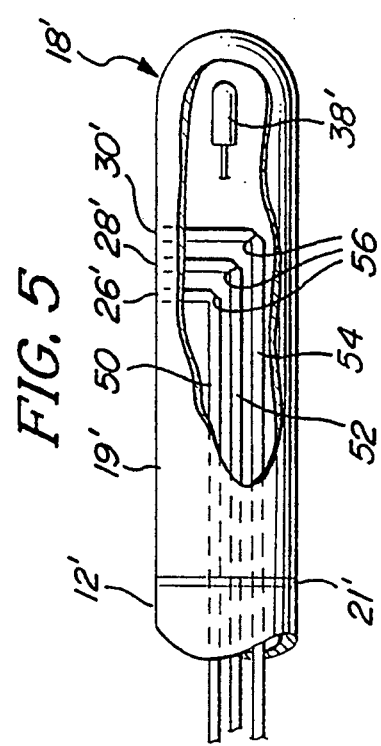

OPTICAL BLOOD OXYGEN SATURATION PROBE FOR INSERTION INTO THE ESOPHAGUS

BACKGROUND OF THE INVENTION

1. Field of the Invention

The present invention generally relates to blood oxygen saturation probes or sensors and, in particular, to blood oxygen saturation probes or sensors which employ an optical technique for sensing the level of blood oxygen saturation.

2. Description of Related Art

The amount of saturation of blood by oxygen is a useful physiologic index of oxygen transport. A variety of techniques have been provided for measuring the level by which arterial blood is saturated by oxygen. The majority of oxygen carried in healthy blood is bound to hemoglobin, the remainder being dissolved in the plasma. Hemoglobin, the oxygen-carrying protein in blood, chemically binds to oxygen atoms and, in doing so, undergoes a change in physical structure which affects the light absorption properties of the hemoglobin.

One technique for measuring oxygen saturation in blood exploits the change in the light absorption properties of hemoglobin to detect the oxygen saturation level optically. With the optical technique, blood, or a portion of tissue carrying blood, is optically illuminated by a sensor or probe connected to an instrument, commonly referred to as an oximeter. The optical blood oxygen saturation measurement is dependent on the relative absorption of infrared light by saturated versus desaturated hemoglobin.

Thus, optical methods of blood oxygen saturation measurement rely on the measurement of transmitted or reflected light through or from a perfused tissue block with the magnitude of the transmitted or reflected light indicating the amount of oxygen bound to hemoglobin. However, the amount of reflected or transmitted light is affected by the total optical path, which is related to the size and absorption of the tissue block and the distance of emitters and sensors from the block. These factors are not controlled at a given anatomical site. Hence, a reference light source of wavelength not absorbed by saturated hemoglobin is used to obtain a baseline signal. Thus, transmitted or reflected light intensity measurements are made using two alternating light sources, one source to establish baseline, and a second source to determine the oxygen saturation.

When the sampling rate of saturation measurement is high enough, real time variation in saturation of blood as it flows through the tissue block is obtainable. The saturation varies as the oxygen is unloaded to the tissue and as fresh oxygenated blood flows into the tissue with each heartbeat. Therefore, pulse rate can be measured from the saturation signal. In addition, correlation of the saturation signal with the pulse signal aids in the determination of the saturation level that is most representative of the arterial blood oxygen saturation.

If saturation waveforms are measured at two sites in the body at different distances from the heart, the time relationship between distinguishing points on the waveforms can be correlated to blood pressure. This measurement requires a physiologically stable monitoring site with ample perfusion.

Heretofore, conventional optical oxygen saturation probes and sensors have not been designed for use in adequately physiologically stable monitoring sites. Rather, the typical optical blood saturation probe is mounted to the surface skin, such as on the chest, finger, or earlobe. Unwanted motion artifacts may appear in the measured oxygen saturation level due to alteration in the optical path and/or peripheral perfusion to the tissue block. Such an externally-mounted sensor or monitor is also susceptible to being accidentally displaced by physicians or other medical personnel working in the vicinity of the patient. Moreover, the tissue near the skin may not be adequately perfused with blood, particularly during physiological stress such as hypothermia or shock.

Other conventional blood oxygen saturation techniques include an intravascular sensor or probe. An intravascular probe is inserted into an artery, particularly the umbilical artery. Although an artery is a more stable site than the skin, the process of inserting an intravascular probe is invasive and is neither convenient for the physician nor completely safe for the patient. Further, to enable intravascular insertion, the blood oxygen saturation sensor must be of extremely small size, a constraint which increases the cost, and decreases the reliability, of the sensor.

Examples of previous oximeters and blood oxygen saturation sensors are provided in U.S. Pat. No. 4,830,014 to Goodman et al., U.S. Pat. No. 5,061,632 to Shepherd et al., and U.S. Pat. No. 4,805,623 to Jöbis. The patent to Shepherd et al. discloses an oximeter with a capillary tube sensor. The patent to Goodman et al. includes a description of the deficiencies of prior art skin-mounted oximeters.

Heretofore, no optical blood oxygen saturation sensors or probes have been developed which have the safety, ease of use, and low cost of an external probe, while also being mountable or insertable to a physiologically stable monitoring site having adequate blood perfusion.

SUMMARY OF THE INVENTION

From the foregoing, it can be appreciated that there is a need to provide an improved optical blood oxygen saturation probe. This object, and other general objects of the invention, are achieved by the provision of a probe sized for insertion into the esophagus of a patient which includes a blood oxygen saturation sensing means for detecting the oxygen saturation level of blood perfusing the tissue of the esophagus.

By providing a blood oxygen saturation sensing means for inserting into the esophagus of a patient, blood oxygen saturation is detected in tissue which provides a physiologically stable monitoring site. When the probe is inserted, preferably into an anesthetized patient, the esophagus of the patient tends to collapse onto the probe, thereby stabilizing the probe. Furthermore, the tissue of the esophagus is highly perfused with blood via small branches of the thoracic aorta and bronchial arteries. Moreover, unlike externally-mounted optical blood oxygen saturation sensors which can be affected by ambient light, the probe of the invention is completely isolated from ambient light, allowing for accurate and precise detection of blood oxygen saturation levels. Hence, the esophagus provides a desirable anatomical site for blood oxygen saturation measurement because of its depth in the body, proximity to the heart, high level of blood perfusion, and physiological stability.

In a preferred embodiment, the probe additionally includes a temperature-sensing means, such as a thermistor or thermocouple, for detecting the internal temperature of the patient, and a heart and respiration sound sensing means for allowing a physician to directly listen to internal heart and respiration sounds.

More specifically, a preferred embodiment comprises an airtight flexible tube having proximal and distal portions, with the distal portion being sized for insertion into the esophagus of a patient. The blood oxygen saturation sensing means includes a pair of light-emitting diodes mounted to a sensor housing attached to the distal portion of the tube. The diodes are oriented for illuminating an interior wall of the esophagus. The blood oxygen saturation sensing means further includes a photodiode mounted to the sensor housing, adjacent to the light-emitting diodes, for receiving light output from the diodes that is reflected from tissue of the wall of the esophagus.

The sound sensing means comprises a flexible membrane mounted externally along an exterior wall of the distal portion of the tube, with a set of apertures being formed in the tube beneath the flexible membrane. In use, the membrane contacts interior walls of the esophagus and vibrates in response to heart and respiration sounds. The distal portion of the tube conducts the heart and respiration sounds to the proximal portion of the tube which is connected via a Luer connector to allow a physician to directly listen to the internal heart and respiration sounds. The temperature-sensing means comprises a thermistor which is mounted within the distal portion of the tube for detecting the temperature of the esophagus in the proximity of the thermistor.

In an alternative embodiment, the blood oxygen saturation sensing means comprises fiber optic light guides extending along the tube from the proximal portion to the distal portion and into the sensor housing. Within the sensor housing, the fiber optic light guides each terminate at a right angle reflector which reflects light transmitted down one of the light guides outwardly into the tissue of the esophagus. Light reflected from the esophagus is received by the second fiber optic light guide and transmitted to the proximal portion of the tube.

In either embodiment, conventional monitoring equipment is provided external to the body for controlling the sensors mounted within the distal portion of the tube and for receiving and processing signals received from the sensors. Connection of the light-emitting diodes, photodetector, and temperature sensor to the monitor's equipment is performed through a cable. In the alternative embodiments, the light sources and photodetector may be placed at the end of the cable with suitable optical connections to the fiber optic light guides.

In any of its embodiments, the invention provides a reliable and accurate sensor for detecting blood oxygen saturation levels. Furthermore, a single probe is provided which yields not only blood oxygen saturation measurements, but also provides temperature measurements and detects heart and respiration sounds. Thus, rather than providing three or four separate probes, as might be required when using the probes and sensors of the prior art, only a single probe is required. Furthermore, because of its simplicity, probes of the invention can be inexpensively constructed for one-time use, then discarded.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1 provides a side elevational view, partially in schematic form, of an esophageal optical blood oxygen saturation probe constructed in accordance with a preferred embodiment of the invention;

FIG. 3 provides a preferred embodiment of an optical blood oxygen saturation sensor portion of the esophageal probe of FIG. 1, which employs light-emitting diodes and photodetectors;

FIG. 4 provides a side view of a heart and respiration sound sensor portion of the esophageal probe of FIG. 1; and FIG. 5 provides an alternative embodiment of the temperature and blood oxygen saturation sensors of the esophageal probe of FIG. 1, employing fiber optic light guides, rather than light-emitting diodes and photodetectors.

DESCRIPTION OF THE PREFERRED EMBODIMENTS

Figure 2:
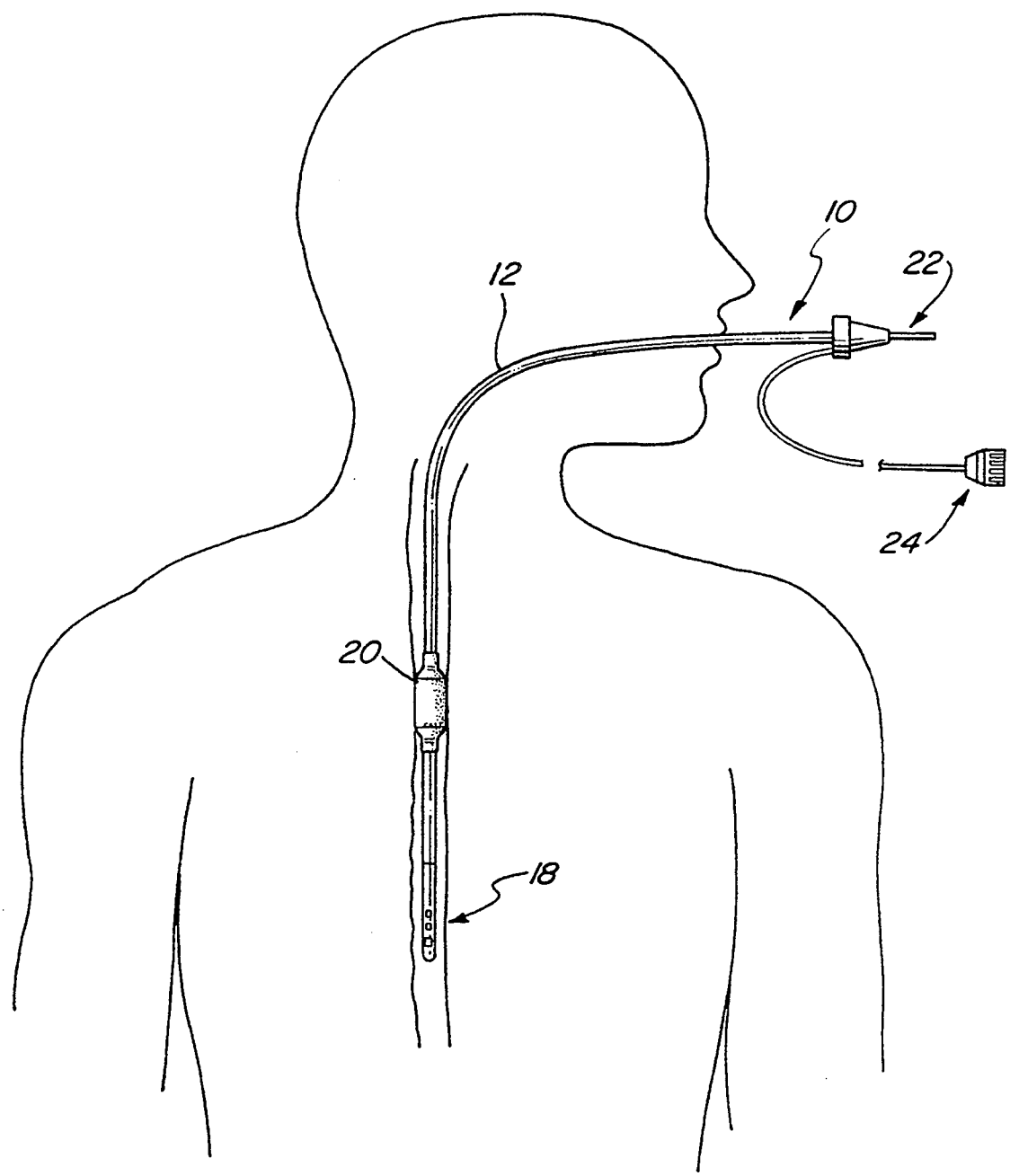
FIG. 2 provides a side view of the esophageal probe of FIG. 1, shown inserted within the esophagus of a patient.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an esophageal optical blood oxygen saturation probe.

Referring to FIGS. 1-4, a preferred embodiment of the invention will now be described. In FIG. 1, an esophageal probe 10 is shown having a flexible tube 12 with a distal end 14 and a proximal end 16. Tube 12, particularly including distal portion 14, is sized for insertion into the esophagus of a patient. Tube 12 is preferably constructed of an airtight, flexible material such as a rubber or flexible polyvinyl chloride material, and is formed with an outside diameter of preferably 0.135 to 0.310 inch. The tube may be somewhat wider or narrower, as desired. However, an outside diameter of greater than ½ inch to 1 inch may be too great to allow for convenient insertion into the esophagus of a patient. Tube 12 may be formed to any of a variety of lengths but is preferably between 19 and 25 inches long. A minimum length of 9 inches may be required to ensure that distal portion 14 can be fully inserted into the esophagus.

Distal portion 14 includes a blood oxygen sensor 18 mounted within a housing 19 and a heart sound and respiration sound sensor 20. Proximal end 16 includes a Luer connector 22 which, as will be described below, allows heart and respiration sounds detected by sound sensor 20 to be transmitted directly into a stethoscope tube for further transmission to a physician's ears or to any form of sound recording or amplifying device (not shown). Also extending from proximal end 16 is an electronic connector 24 which allows optical blood saturation sensor 18 to be electronically connected to an external oxygen saturation monitor (not shown) via a set of wires extending internally along the length of tube 12. For clarity, these wires are not shown in FIG. 1.

In use, the distal portion 14 of esophageal probe 10 is inserted into the esophagus of a patient. As it is inserted, internal walls of the esophagus responsively collapse onto the outer surface of tube 12 and onto the outer surfaces of housing 19 and heart and respiration sound sensor 20. This collapse, or slight contraction, holds tube 12 and housing 19 in position such that neither sensor 18 nor 20 moves appreciably with respect to the esophagus.

The mounting position of probe 10 within the esophagus is shown within FIG. 2. As can be seen from FIG. 2, both the oxygen saturation sensor 18 and the heart and respiration sound sensor 20 are positioned within the esophagus to a fairly substantial depth, where they are isolated from external sounds and light, thus allowing the sensors to obtain precise measurements unaffected by the ambient light or sounds around the patient. Preferably, the patient is anesthetized prior to insertion of probe 10 into the esophagus.

The construction and operation of blood oxygen saturation 18 and heart and respiration sound sensor 20 will be described more fully below with reference to FIGS. 3 and 4. For the purposes of FIG. 2, it is sufficient to note that blood oxygen saturation sensor 18 is an optical sensor which illuminates tissue of the esophagus with an alternating set of optical frequencies, and includes a photodetector for receiving light reflected from the tissue of the esophagus. An electrical signal, generated in response to the magnitude of the detected light, is transmitted from the blood oxygen saturation sensor 18 to the proximal end 16 of probe 10, where it is connected to an external monitor via electrical connector 14 (FIG. 1).

In accordance with conventional techniques, the external monitor compares the magnitude of signals from the photodetector in response to reflected light from the two light sources. The photodetector and light sources are located in the tip of the esophageal stethoscope comprised of a sensor assembly 18. Since the tissue of the esophagus is perfused with blood, the relative amount of light detected by sensor 18 is affected by the amount of oxygen bound to hemoglobin within the blood of the perfused tissue. To obtain a baseline, blood oxygen sensor 18 also illuminates the esophagus tissue with a frequency of light which is not absorbed by saturated hemoglobin. By comparing the light received from the baseline nonabsorbed frequency and the received light from the absorbed frequency, the external monitor determines the blood oxygen saturation level of the blood perfusing the tissue of the esophagus. The use of two frequencies also adequately compensates for the presence of liquids in the esophagus.

Sound sensor 20 detects internal sounds within the esophagus, particularly heart and respiration sounds. As will be discussed more fully below, the sensed sounds are transmitted up tube 12 to proximal end 16, where they are transmitted through connector 22 into an extension tube (not shown) for direct transmission to the ears of a physician. Hence, the physician can directly monitor the internal heart and respiration sounds while blood oxygen saturation measurements are simultaneously performed.

By inserting the blood oxygen saturation sensor and the heart and respiration sound sensor into the esophagus, the sensors are not only isolated from ambient light and noises external to the patient, but are stably positioned such that they are not moved relative to the body, either by the movement of the patient or by the activity of physicians and other medical personnel in the vicinity of the patient.

The construction of blood oxygen saturation sensor 18 will now be described in more detail with reference to FIG. 3. In FIG. 3, an extreme end of distal portion 14 of tube 12 is shown in an enlarged view, with internal wires 42 which connect components of sensor 18 to connector 24 (FIG. 1) shown in phantom lines. Blood oxygen sensor 18 is mounted within housing 19 which is attached, at 21, to the distal end of tube 12. Housing 19 is preferably formed of a plastic material. A wire mounting bracket 23 is provided within housing 19 for feeding the internal wires into a single cable of wires 42. A variety of means may be employed for connecting housing 19 to tube 12. Preferably, however, the distal portion of tube 12 is adhesively affixed to housing 19.

Blood oxygen sensor 18 includes a pair of light-emitting diodes 26 and 28, each of which is mounted within apertures formed in housing 19 such that light emitted from the light-emitting diodes illuminates tissue of the esophagus adjacent to tube 12. Alternatively, diodes 26 and 28 can be mounted externally to housing 19 or adjacent to a transparent aperture within housing 19. Preferably, diodes 26 and 28 are mounted adjacent to each other, as shown. Also in proximity to diodes 26 and 28 is a photodetector 30. Photodetector 30 and light-emitting diodes 26 and 28 are of conventional construction and may be similar to diodes and photodetectors used in conventional external blood oxygen saturation probes.

Light-emitting diode 26 emits light at a frequency absorbed by hemoglobin bound to blood. Light-emitting diode 28 outputs light at a frequency which is not absorbed by the hemoglobin. Photodetector 30 detects light at both of the above-described frequencies. Light-emitting diode 26 is connected to external control circuitry via a wire 32 which extends along the length of tube 12 to connector 24 (FIG. 1). Likewise, light-emitting diode 28 is electrically connected to the external control circuitry via a wire 34 which extends internally along the length of tube 12 to electrical connector 24. The external control circuit (not shown) transmits signals along lines 32 and 34 to diodes 26 and 28 to alternatingly illuminate the diodes to thereby illuminate the tissue of the esophagus. A third wire connects photodetector 30 to the external control circuit. Additional wires (not shown) are connected to light-emitting diodes 26 and 28 and photodetector 30 for current or signal return and extended along the length of tube 12 to connector 24. Photodetector 30 generates an electrical signal in response to light which is output from diodes 26 and 28 and subsequently reflected from the tissue of the esophagus. The light-responsive signal is transmitted along wire 36 and through connector 24 (FIG. 1) to the external control circuit and monitor. As noted above, the monitor compares the magnitude signals from the photo-detector in response to reflected light from the two light sources. Photodetector 30 may be either mounted externally to tube 12, mounted within an aperture formed in tube 12, or mounted internally adjacent to a substantially transparent aperture formed along tube 12. Additional wires (not shown) are connected to light-emitting diodes 26 and 28 and photodetector 30 for current or signal return and extended along the length of tube 12 to connector 24.

Also included within housing 19 adjacent to blood oxygen sensor 18 is a thermistor or thermocouple temperature sensor 38. Temperature sensor 38 is of conventional design and is preferably mounted within housing 19 for electrically detecting the temperature within the esophagus. Temperature sensor 38 is connected to a pair of wires 40 which extend internally along the length of tube 12 and are connected via connector 24 (FIG. 1) to an external temperature circuit. Although shown mounted within housing 19, temperature sensor 38 may alternatively be mounted along the length of tube 12 so long as it can be inserted within the esophagus to detect internal body temperature. However, the mounting of temperature sensor 38 in proximity to the components of blood oxygen sensor 18 is preferred. Wires 32, 34, 36, and 40, and others not shown are bundled together into the single cable of wires 42, which extends internally within tube 12 and connects to connector 24.

Heart and respiration sound sensor 20 is shown more fully in FIG. 4. Sound sensor 20 includes a membrane 44 formed of a flexible airtight material such as rubber or a flexible plastic. Membrane 44 is generally cylindrical and includes opposing ends 46 and 48 which are mounted to an outside surface of tube 12. Membrane 44 normally collapses onto tube 12 under pressure from the internal walls of the esophagus. A set of apertures 49 are formed within tube 12 beneath membrane 44. With membrane 44 in direct physical contact with the inner walls of the esophagus, as shown in FIG. 2, internal sound vibrations within a patient caused by heart and respiration of the patient cause membrane 44 to vibrate which, in turn, causes air within tube 12 to responsively vibrate. In this manner, internal heart and respiration sounds are transferred through membrane 44 and conducted into tube 12 via apertures 49. Within tube 12, the sound vibrations are conducted to proximal end 16 of tube 12, where they are fed through Luer connector 22 into an extension tube (not shown) so that the physician can directly hear the internal heart and respiration sounds of the patient. Alternatively, internal sounds detected by sensor 20 may be transmitted to any form of external sound detecting or recording device.

FIG. 5 provides an alternative embodiment of probe 10 with like elements represented by like reference numerals with primes attached. In FIG. 5, a housing 19' is shown mounted to a distal portion of tube 12'. A temperature sensor 18' is mounted within housing 19' for detecting the temperature within the esophagus of the patient. However, unlike the embodiment of FIGS. 1–4 where a pair of light-emitting diodes are used in conjunction with a photodetector for detecting blood oxygen saturation, probe 10' of FIG. 5 includes a set of three fiber optic light guides 50, 52, and 54. Each fiber optic light guide 50, 52, and 54 extends along the length of tube 12' from a proximal portion, similar to that shown in FIG. 1, to housing 19' shown in FIG. 5. An end of each fiber optic light guide includes a right angle reflector 56 for reflecting light transmitted along the light guide to a direction perpendicular to that of the light guide. Right angle reflectors 56 allow light transmitted down the length of tube 12' to be reflected perpendicularly onto the internal side wall of the esophagus. A set of substantially transparent apertures are formed along a side wall of housing 19' adjacent to right angle reflectors 56 to allow light reflected by the right angle reflectors to reach the internal side wall of the esophagus.

First and second light guides 50 and 52 are analogous to the light-emitting diodes 26 and 28 of FIGS. 1–4, and the exit apertures of these light guides are respectively denoted 26' and 28'. First light guide 50 transmits a light having a frequency absorbed by saturated hemoglobin, whereas light guide 52 transmits a light having a frequency which is not absorbed by saturated hemoglobin. Light guide 56 is analogous to photodetector 30 of the embodiment of FIGS. 1–4, and its entrance aperture is denoted 30'. Light guide 56 receives light reflected from the tissue of the esophagus and transmits the light to the proximal end of probe 10' for eventual transmission to an external blood oxygen saturation monitor. In this embodiment, light sources analogous to light-emitting diodes 26 and 28 and photodetectors analogous to 30 may be located in the saturation monitor or at the end of the cable (not shown) interconnecting the probe and the saturation monitor. In this embodiment, light sources analogous to light-emitting diodes 26 and 28 and photodetector analogous to 30 may be located in the saturation monitor or at the end of the cable (not shown) interconnecting the probe and the saturation monitor. Thus, fiber optic light guides 50 and 52 alternatingly provide pulses of light at two different frequencies, and light guide 56 receives reflected light and transmits that light to an external monitor. Although shown as having right angle reflectors 56, each fiber optic light guide 50, 52, and 54 can alternatively be bent at right angles to directly illuminate, or receive illumination from, the internal wall of the esophagus. Right angle reflectors are preferred, since housing 19' may be of such a narrow width that it is impractical to turn the ends of the fiber optic light guides through a full 90 degrees.

In another alternative embodiment, the fiber optic light guides are oriented to transmit light at an angle other than the perpendicular from the side of housing 19'. In such an embodiment, it may be necessary to increase the output luminosity of light guides 50 and 52 to compensate for any light lost due to the nonperpendicular transmission angle of the light guides.

A temperature sensor 38' is provided for measuring temperature. Although temperature sensor 38' may be an electrical thermistor such as the one described above with reference to the embodiment of FIGS. 1–4, temperature sensor 38' may be alternatively replaced with a fiber optic optical temperature sensor (not shown). In such an embodiment, one or more additional fiber optic light guides extend along the length of tube 12' for transmitting and receiving light at a frequency suited for the optical detection of the temperature of the esophagus. Such an optical temperature sensor is connected to conventional optical temperature-sensing means mounted externally to the probe assembly.

In any of its embodiments, the invention provides a compact and inexpensive probe for detecting the blood oxygen saturation of tissue of the esophagus. By mounting an optical blood oxygen saturation sensor to an esophageal probe, blood oxygen saturation detection is performed at a physiologically stable environment completely isolated from external ambient light. Furthermore, because the tissue of the esophagus is well perfused with blood, a more precise and reliable measurement is made of the blood oxygen saturation than can be achieved with conventional externally-mounted sensors such as those mounted to the chest or earlobe of a patient.

The above-described heart and respiration sound sensor and temperature sensor need not be provided in combination with the blood oxygen saturation sensor, but such combination is desirable, since the combination provides a single probe with the capability of performing a number of useful measurements. Hence, only a single probe need be provided, rather than a set of two or three separate probes. Preferably, the entire probe is inexpensively constructed for one-time use. Thus, after insertion into a patient for detecting the blood oxygen saturation level, as well as the body temperature and heart and respiration sounds, the probe is withdrawn from the esophagus, disconnected from external monitors, then simply discarded.

Although shown and described as having control circuit means which are entirely separate from probe 10, the probe may alternatively be constructed with control circuits mounted within the probe, particularly within the distal portion. Thus, if desired, electronic circuitry for controlling the light-emitting diodes and the photo-detector of the embodiment of FIGS. 1-4 can be mounted within the housing of the blood oxygen saturation sensor. Furthermore, a variety of transmission or connection mechanisms can be used for connecting the various sensors to external monitors. The electrical wires or optical light guides described above are preferred because of their reliability and ease and inexpensive construction.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A probe insertable into the esophagus comprising:
    a tubular member, said tubular member being airtight and flexible, having a proximal and a distal portion with the distal portion being sized for insertion into the esophagus of a patient;
    a flexible membrane, said tubular member extending to and beyond said flexible membrane and passing centrally thereof, said flexible membrane surrounding and extending away from said tubular member, a set of apertures formed in a side wall of said tubular member beneath said flexible membrane, said membrane vibrating in response to internal heart and respiration sounds of said patient, said tubular member conducting said sounds to said proximal portion;
    optical blood oxygen saturation sensing means, located at and integral to said distal portion of said tubular member, for determining the oxygen saturation of blood perfusing tissues of the esophagus without contacting said blood, said means comprising a first light source emitting light of wavelength not absorbed by saturated hemoglobin, said first light source oriented to transmit light at an angle other than the perpendicular from the side wall of said tubular member, a second light source emitting light of wavelength absorbed by saturated hemoglobin, said second light source oriented to transmit light at an angle other than the perpendicular from the side wall of said tubular member; and a sensor means for receiving light reflected from the tissue of the esophagus, said sensor means oriented to receive light at an angle other than the perpendicular from the side wall of said tubular member; and
    signal transmission means, extending along the interior of said tubular member between said blood oxygen saturation sensing means and said proximal portion of said tubular member, for transmitting an input signal to said sensing means and for transmitting an output signal from said sensing means, the input signal providing for the projection of light onto the tissues of the esophagus and the output signal being responsive to light reflected by said tissues.

2. The esophageal probe of claim 1, wherein the blood oxygen saturation sensing means and signal transmission means comprise:
    a pair of light-emitting diodes integral to said distal portion of said tube and connected to said proximal portion by electrical conductors which transmit an electrical signal for illuminating said diodes, said diodes being oriented for illuminating said tissues of said esophagus; and
    a photodiode mounted in proximity to said light-emitting diodes for receiving light produced by said diodes reflected from said tissues, the photodiode being connected to said proximal portion by electrical conductors which transmit an electrical signal responsive to light received by said photodiode.

3. The esophageal probe of claim 1, wherein the blood oxygen saturation sensing means and the signal transmission means comprise:
    a first and a second fiber optic light guides for transmitting light from said proximal portion to said distal portion of said tube, wherein distal ends of said first and second light guides are oriented for illuminating said tissues of the esophagus; and
    a third fiber optic light guide for transmitting light from said housing to said proximal portion of said tube, wherein a distal portion of the third light guide is oriented for receiving light reflected from said tissues of the esophagus and transmitting said light to said proximal portion of said tube.

4. The esophageal probe of claim 1, further comprising a temperature sensing means for detecting the temperature of said esophagus proximal to said temperature sensing means.

5. The esophageal probe of claim 4, wherein the temperature sensing means is an electrical temperature sensing device.

6. The esophageal probe of claim 4, wherein the temperature sensing means is an optical temperature sensing device.

* * * * *